(12) United States Patent  
Ford et al.

(10) Patent No.: US 8,530,525 B2  
(45) Date of Patent: Sep. 10, 2013

(54) METHODS AND COMPOSITIONS FOR PROTECTING AND TREATING NEUROINJURY

(75) Inventors: Byron D. Ford, Atlanta, GA (US); Peter A. Ferchmin, San Juan, PR (US); Vesna A. Eterovic, San Juan, PR (US)

(73) Assignees: Morehouse School of Medicine, Atlanta, GA (US); Universidad Central Del Caribe of Bayamon, Bayamon, PR (US)

( * ) Notice: Subject to any disclaimer, the term of this patent is extended or adjusted under 35 U.S.C. 154(b) by 322 days.

(21) Appl. No.: 12/829,056

(22) Filed: Jul. 1, 2010

(65) Prior Publication Data

US 2011/0015186 A1    Jan. 20, 2011

Related U.S. Application Data

(60) Provisional application No. 61/225,341, filed on Jul. 14, 2009.

(51) Int. Cl.  
*A61K 31/045* (2006.01)

(52) U.S. Cl.  
USPC .......................................................... 514/729

(58) Field of Classification Search  
USPC .......................................................... 514/729  
See application file for complete search history.

(56) References Cited

U.S. PATENT DOCUMENTS

| 4,916,160 | A | 4/1990 | Morita et al. |
| 6,204,289 | B1 | 3/2001 | Eterovic et al. |
| 6,489,357 | B1 | 12/2002 | Eterovic et al. |
| 2004/0092583 | A1 | 5/2004 | Shanahan-Prendergast |
| 2005/0250752 | A1 | 11/2005 | Ziawiony et al. |

FOREIGN PATENT DOCUMENTS

WO    WO2008/002594 A2    1/2008

OTHER PUBLICATIONS

Shih TM, McDonough JH Jr. Neurochemical mechanisms in soman-induced seizures. J Appl Toxicol. Jul.-Aug. 1997;17(4):255-64.*  
Smulders CJ, Bueters TJ, Vailati S, van Kleef RG, Vijverberg HP. Block of neuronal nicotinic acetylcholine receptors by organophosphate insecticides. Toxicol Sci. Dec. 2004;82(2):545-54. Epub Sep. 1, 2004.*  
Worek F, Widmann R, Knopff O, Szinicz L. Reactivating potency of obidoxime, pralidoxime, HI 6 and HLö 7 in human erythrocyte acetylcholinesterase inhibited by highly toxic organophosphorus compounds. Arch Toxicol. Mar. 1998;72(4):237-43.*  
Mehrani H, Golmanesh L. Evaluation of nicotinic receptors agonists and antagonists against paraoxon exposed PC12 cells. Environ Toxicol Pharmacol. Jul. 2008;26(1):22-9. doi: 10.1016/j.etap.2008. 01.003. Epub Jan. 18, 2008.*  
International Search Report (International Application No. PCT/US2010/040903, filed Jul. 2, 2010).

(Continued)

*Primary Examiner* — Paul Zarek  
(74) *Attorney, Agent, or Firm* — Ping Wang; Andrews Kurth LLP

(57) ABSTRACT

A method and composition for protecting and/or treating neuroinjury are disclosed. In one aspect, the present application discloses a method for protecting and/or treating a subject from organophosphate-induced neuronal injury. The method comprises administering to a subject an effective amount of 4R cembranoid, 4S cembranoid or a cembranoid analogue. In another aspect, the application discloses neuroprotective pharmaceutical compositions for protecting and/or treating a subject from organophosphate-induced neuronal injury. A kit for protecting and treating a subject from organophosphate-induced neurodamage is also disclosed.

9 Claims, 10 Drawing Sheets  
(9 of 10 Drawing Sheet(s) Filed in Color)

(56) References Cited

OTHER PUBLICATIONS

Written Opinion of the International Search Authority (International Application No. PCT/US2010/040903, filed Jul. 2, 2010).
Ferchmin, P.A., et al., "Actions of Octocoral and Tobacco Cembranoids on Nicotinic Receptors", Toxicon., vol. 54, pp. 1174-1182 (2009).
Ferchmin, P.A., et al., "Tobacco cembranoids protect the function of acute hippocampal slices against NMDA by a mechanism mediated by alpha4beta2 nicotinic receptors", J Neurosci Res., vol. 82, pp. 631-641 (2005).
Andersen, P., et al, Unit analysis of hippocampal polulation spikes. Exp Brain Res, 1971. 13(2): p. 208-221.
Bakry, N.M., et al., Direct actions of organophosphate anticholinesterases on nicotinic and muscarinic acetylcholine receptors. J Biochem Toxicol, 1988. 3: p. 235-259.
Bi, R, et al. The tyrosine kinase and mitogen-activated protein kinase pathways mediate multiple effects of estrogen in hippocampus, Neuroscience Program 2000, vol. 97 No. 7, p. 3602-3607.
Carlson, K., et al, Organophosphorus compound-induced apoptosis in SH-SY5Y human neuroblastoma cells. Toxicol Appl Pharmacol, 2000. 168(2): p. 102-113.
Caughlan, A. et al., Chlorpyrifos induces apoptosis in rat cortical neurons that is regulated by a balance between p38 and ERK/JNK MAP kinases. Toxicol Sci, 2004. 78(1): p. 125-134.
Chebabo, S.R., et al, The organophosphate sarin, at low concentrations, inhibits the evoked release of GABA in rat hippocampal slices. Neurotoxicology, 1999. 20(6): p. 871-882.
Chi, M, et al, Action of organophosphate anticholinesterases on the three conformational states of nicotinic receptor. Adv Exp Med Biol, 1995. 363: p. 65-73.
Dunham, N.W., et al, A note on a simple apparatus for detecting neurological deficit in rats and mice. J Am Pharm Assoc Am Pharm Assoc (Baltim), 1957. 46(3): p. 208-209.
Dunn, M.A., et al, Progress in medical defense against nerve agents. Jama, 1989. 262(5): p. 649-652.
El Saved, K.A. et al., Biocatalytic and semisynthetic studies of the anticancer tobacco cembranoids. Expert Opin Investig Drugs, 2007. 16(6): p. 877-887.
Fahmy, H., et al, Potent Skin Cancer Chemopreventing Activity of Some Novel Semi-synthetic Cembranoids from Marine Sources. Marine Drugs, 2006. 4(2): p. 28-36.
Ferchmin, P.A., et al, Tobacco cembranoids protect the function of acute hippocampal slices against NMDA by a mechanism mediated by alpha4beta2 nicotinic receptors. J Neurosci Res, 2005.
Ferchmin, P.A., et al, Tobacco cembranoids block behavioral sensitization to nicotine and inhibit neuronal acetylcholine receptor function. J Neurosci Res, 2001. 64(1): p. 18-25.
Ferchmin, P.A., et al, Spermine is neuroprotective against anoxia and N-methyl-D-aspartate in hippocampal slices. Brain Res, 2000. 859(2): p. 273-279.
Ferchmin, P.A., et al, Nicotinic receptors differentially regulate N-methyl-D-aspartate damage in acute hippocampal slices. J Pharmacol Exp Ther, 2003. 305(3): p. 1071-1078.
Ferchmin, P.A., et al, alpha-Difluoromethylornithine does not antagonize the behavioral effects of putrescine. Pharmacol Biochem Behav, 1993. 45(4): p. 967-971.
Fryer, A.D., et al, Mechanisms of organophosphate insecticide-induced airway hyperreactivity. Am J Physiol Lung Cell Mol Physiol, 2004. 286(5): p. L963-969.
Gant, D.B., et al, Action of organophosphates on GABAA receptor and voltage-dependent chloride channels. Fundam Appl Toxicol, 1987. 9(4): p. 698-704.
Iwamaru, A., et al, Eupalmerin acetate, a novel anticancer agent from Caribbean gorgonian octocorals, induces apoptosis in malignant glioma cells via the c-Jun NH2-terminal kinase pathway. 2007. p. 184-192.
de Olmos et al., Use of an amino-cupric-silver technique for the detection of early and semiacute neuronal degeneration caused by neurotoxicants, hypoxia, and physical trauma, Neurotoxicol Teratol (1994) (Abstract).

Douen et al., Regulation of nestin expression after cortical ablation in adult rat brain, (2004) Brain Research 1008:139-146 (Abstract).
Eaton, M.J., et al, Differential inhibition of nicotine- and acetylcholine-evoked currents through alpha4beta2 neuronal nicotinic receptors by tobacco cembranoids in Xenopus oocytes. Neurosci Lett, 2004. 366(1): p. 97-102.
Kassa, J. et al, A comparison of the potency of newly developed oximes (K074, K075) and commonly used oximes (obidoxime, HI-6) to counteract tabun-induced neurotoxicity in rats. Toxicology, 2007. 229(1-2): p. 136-144.
Leikin, J.B., et al, A review of nerve agent exposure for the critical care physician. Crit Care Med, 2002. 30(10): p. 2346-2354.
Lein, P.J. et al, Organophosphorus Insecticides Induce Airway Hyperreactivity by Decreasing Neuronal M2 Muscarinic Receptor Function Independent of Acetylcholinesterase Inhibition. Toxicol. Sci., 2005. 83(1): p. 166-176.
Lemercier, G., P. et al, Histological and histochemical changes in the central nervous system of the rat poisoned by an irreversible anticholinesterase organophosphorus compound. Acta Neuropathol, 1983. 61(2): p. 123-9.
Martin, C.O., et al, Neurological aspects of biological and chemical terrorism: a review for neurologists. Arch Neurol, 2003. 60(1): p. 21-25.
McDonough, J.H., Jr., et al, Brain regional glucose use during Soman-induced seizures. Neurotoxicology, 1983. 4(2): p. 203-10.
McDonough, J.H., Jr., et al, Direct microinjection of soman or VX into the amygdala produces repetitive limbic convulsions and neuropathology. Brain Res, 1987. 435(1-2): p. 123-37.
McLeod, C.G., Jr., et al, Acute neuropathology in soman poisoned rats. Neurotoxicology, 1984. 5(2): p. 53-57.
Newmark, J., Therapy for nerve agent poisoning. Arch Neurol, 2004. 61(5): p. 649-652.
Okudera, H., Clinical features on nerve gas terrorism in Matsumoto. J Clin Neurosci, 2002. 9(1): p. 17-21.
Olsson, E., et al, Structure-related inhibiting activity of some tobacco cembranoids on the prostaglandin synthesis in vitro. Planta Med, 1993. 59(4): p. 293-295.
O'Neill, J.J., Non-cholinesterase effects of anticholinesterases. Fundam Appl Toxicol, 1981. 1(2): p. 154-160.
Pagan, O.R., et al, Cembranoid and long-chain alkanol sites on the nicotinic acetylcholine receptor and their allosteric interaction. Biochemistry, 2001. 40(37): p. 11121-11130.
Petras, J.M., Soman neurotoxicity. Fundam Appl Toxicol, 1981, 1(2): p. 242.
Petras, J.M., Neurology and neuropathology of Soman-induced brain injury: an overview. J Exp Anal Behav, 1994. 61(2): p. 319-29.
Petroianu, G.A., et al, New K-Oximes (K-27 and K-48) in Comparison with Obidoxime (LuH-6), HI-6, Trimedoxime (TMB-4), and Pralidoxime (2-PAM): Survival in Rats Exposed IP to the Organophosphate Paraoxon. Toxicology Mechanisms and Methods, 2007, 17(7): p. 401-408.
Saito, Y., et al, Identification of cembratriene-4,6-diol as antitumor-promoting agent from cigarette smoke condensate. Carcinogenesis, 1985. 6(8): p. 1189-94.
Schurr, A., et al, Hypoxia, excitotoxicity, and neuroprotection in the hippocampal slice preparation. J Neurosci Methods, 1995. 59(1): p. 129-38.
Schurr, A., et al, Protection by MK-801 against hypoxia-, excitotoxin-, and depolarization-induced neuronal damage in vitro. Neurochem Int, 1995. 26(5): p. 519-525.
Schurr, A., et al, Cerebral ischemia revisited: new insights as revealed using in vitro brain slice preparations. Experientia, 1989. 45(8): p. 684-695.
Shih, T.M., et al, Control of nerve agent-induced seizures is critical for neuroprotection and survival. Toxicol Appl Pharmacol, 2003. 188(2): p. 69-80.
Small, D.L., et al, Identification of calcium channels involved in neuronal injury in rat hippocampal slices subjected to oxygen and glucose deprivation. Brain Res, 1997. 753(2): p. 209-218.
Sogorb, M.A., et al, Future applications of phosphotriesterases in the prophylaxis and treatment of organophosporus insecticide and nerve agent poisonings. Toxicol Lett, 2004. 151(1): p. 219-233.

Solberg, Y.,et al, The role of excitotoxicity in organophosphorous nerve agents central poisoning. Trends Pharmacol Sci, 1997. 18(6): p. 183-185.

Stables, J.P. et al, The NIH Anticonvulsant Drug Development(ADD) Program: preclinical anticonvulsant screening project. 1997, p. 1-9.

Tang, H.W., et al, Inhibition by soman of NMDA-stimulated [3H]norepinephrine release from rat cortical slices, studies of non-cholinergic effect. Brain Res, 1998. 787(1): p. 123-131.

Tashma, Z., et al, Bretazenil, a benzodiazepine receptor partial agonist, as an adjunct in the prophylactic treatment of OP poisoning. J Appl Toxicol, 2001.21 Suppl 1: p. S115-119.

Van Meter, W.G., et al, CNS effects of anticholinesterases in the presence of inhibited cholinesterases. Arch Int Pharmacodyn Ther, 1978. 231(2): p. 249-260.

Ogita et al., "In vivo neuroprotective role of NMDA receptors against kainate-induced excitotoxicity in murine hippocampal pyramidal neurons," Journal of Neurochemistry, 2003, pp. 1336-1346, vol. 85.

Coupland, R., et al, Science and Prohibited Weapons. Science, 2005. 308(5730): p. 1841.

Kamel, F. et al, Association of pesticide exposure with neurologic dysfunction and disease. Environ Health Perspect 2004. 112(9): p. 950-958.

Walley, T.J., et al, The haemodynamic effects of intravenous nifedipine in normotensive and hypertensive subjects. J Hum Hypertens, 1988. 2(3): p. 199-202.

Wallis, R.A. et al, Delayed neuronal injury induced by sub-lethal NMDA exposure in the hippocampal slice. Brain Res., 1995. 674(1): p. 75-81.

Wang, T., et al, Thiopental attenuates hypoxic changes of electrophysiology, biochemistry, and morphology in rat hippocampal slice CA1 pyramidal cells. Stroke, 1999. 30(11): p. 2400-2407.

Weitberg, A.B. et al, The effect of epigallocatechin galleate and sarcophytol A on DNA strand breakage induced by tobacco-specific nitrosamines and stimulated human phagocytes. J Exp Clin Cancer Res, 1999. 18(3): p. 433-437.

Wu, X., et al, Inhibition of N-methyl-D-aspartate receptors increases paraoxon-induced apoptosis in cultured neurons. Toxicol Appl Pharmacol, 2005. 208(1): p. 57-67.

Yarowsky, P., et al, Noncholinesterase actions of an irreversible acetylcholinesterase inhibitor on synaptic transmission and membrane properties in autonomic ganglia. Cell Mol Neurobiol, 1984. 4(4): p. 351-66.

Yin, W., et al, Preconditioning suppresses inflammation in neonatal hypoxic ischemia via Akt activation. Stroke, 2007. 38(3): p. 1017-1024.

Zhang, Y. et al, Cytosolic Ca2+ changes during in vitro ischemia in rat hippocampal slices: major roles for glutamate and Na+-dependent Ca2+ release from mitochondria. J.Neurosci., 1999. 19(9): p. 3307-3315.

* cited by examiner

A.

B.

A.

B.

C.

24h after DFP
Amino cupric silver 48h after DFP
Amino cupric silver 24h after DFP
Nestin 48h after DFP
Nestin

METHODS AND COMPOSITIONS FOR PROTECTING AND TREATING NEUROINJURY

This application claims priority from U.S. Provisional Application Ser. No. 61/225,341, filed Jul. 14, 2009. The entirety of that provisional application is incorporated herein by reference.

FIELD

This application generally relates to the field of medical prevention and treatment; in particular, relates to the prevention and treatment of a neuroinjury.

BACKGROUND

Organophosphorus (OP) nerve toxins bind to and inactivate acetylcholinesterase (AChE). The inactivation of AChE produces a supra-physiological accumulation of acetylcholine (ACh) at peripheral and central nervous system muscarinic and nicotinic synapses. The excess of ACh causes the release of other transmitters that are normally regulated by ACh.

OP nerve agents stimulate all cholinergic synapses essentially simultaneously. Because ACh is one of the most widely distributed neurotransmitters in the brain, a large nerve agent challenge will cause a rapid loss of consciousness, seizures, and inhibition of the medullary respiratory center. Therefore, death from OP poisoning is usually caused by respiratory failure (Newmark J (2004) Arch Neurol 61:649-652).

The areas most prominently and consistently affected are the cerebral cortex, amygdala, hippocampus, basal ganglia, and various thalamic nuclei McDonough et al. (1987) Brain Res 435:123-137; Petras J M (1994) *J Exp Anal Behav* 61:319-329.

Recent in vitro studies demonstrated that OPs can also cause neuronal apoptosis. For example, Caughlan et al. reported that chlorpyrifos induce apoptosis in primary cortical neurons cultured from embryonic or newborn rats (Caughlan A, et al. (2004) Toxicol Sci 78:125-134). They further concluded that the chlorpyrifos-induced apoptosis occurred independently of AChE inhibition. Another OP pesticide, paraoxon, was shown to induce apoptosis in cultured cerebellar granule cells and in a human neuroblastoma cell line (Carlson K, et al. (2000) *Toxicol Appl Phartnaeol* 168: 102-113; Wu X, et al. (2005) *Toxicol Appl Pharmacol* 208: 57-67).

The classical treatments for OP exposures include: (1) protection of muscarinic ACh receptors by the non-selective muscarinic antagonist atropine, (2) reactivation of inhibited AChE through the use of oximes, and (3) protection against central nervous system seizures with benzodiazepines. However, the traditional and many of the newer pharmacological treatments are based on the administration of drugs with an intrinsic neurotoxicity or insufficient capacity to protect neurons in the PNS or CNS. For example, atropine reverses cholinergic crisis at muscarinic synapses, but because atropine is inactive at muscle nicotinic receptors, neuromuscular symptoms such as twitching and incoordination are not addressed.

Oximes have proven effective in reducing OPs-mediated deaths but their protection is limited. Oximes have a narrow time window to regenerate the AChE. Sometime after the OP binds to AChE, the addition compound "ages" by loosing a side chain in a process called "aging." Aging makes the OP-AChE addition compound immune to oxime.

Diazepam and its more effective analogue, midazolam, are anticonvulsants effective against seizures induced by OPs. Exposure to OP nerve agents induces cholinergically mediated seizures, and later, glutamate released by the ACh accumulation generalizes the seizures. Glutamate-sustained seizures are a major factor in mediating CNS damage by OP-triggered seizures (Solberg Y, et al. (1997) *Trends Pharmacol Sci* 18:183-185). NMDA antagonists were shown to be neuroprotective against OP-induced seizures and the subsequent neuropathology. Therefore, NMDA receptor antagonists were proposed as potential therapy for OP-induced CNS toxicity. However, recent studies have shown that the NMDA receptor antagonist, MK-801, enhances paraoxon-mediated neurotoxicity and apoptosis in vitro, suggesting that the activity of the NMDA receptor is important to maintain the survival of neurons exposed to OPs (Wu X, et al. (2005) *Toxicol Appl Pharmacol* 208:57-67). In addition, NMDA antagonists induce severe psychotropic side effects in patients.

Pyridostigmine bromide is used as a prophylactic treatment in scenarios where there is a risk of exposure to OP nerve agents. This compound was used by Allied troops in the first Gulf War. About half of the military personnel receiving the pre-treatment complained of symptoms, including exacerbation of asthma, hypertension, allergic reactions, and intolerable gastrointestinal pain (Dunn M A, et al. (1989) *Jama* 262:649-652). Since their return, many military personnel have also complained of neurological symptoms. The cause of these symptoms is unknown, but prophylactic pyridostigmine treatment, along with exposure to OP pesticides, is considered to be a possible contributor (Leikin J B, et al. (2002) *A Grit Care Med* 30:2346-2354).

SUMMARY

One aspect of the present invention relates to a method for protecting a subject from OP-induced neuronal injury. The method comprises administering to a subject an effective amount of 4R cembranoid, 4S cembranoid or a cembranoid analogue.

In a related embodiment, the neuronal injury is brain injury. In another embodiment, the 4R cembranoid, 4S cembranoid or cembranoid analogue is administered prior to, or immediately after, an exposure to an OP-containing agent. In a preferred embodiment, 4R cembranoid is administered prior to, or immediately after, an exposure to an OP-containing agent.

In another embodiment, the 4R cembranoid, 4S cembranoid or cembranoid analogue is administered in the dose range of 0.002-10 mg/kg body weight.

In another embodiment, the 4R cembranoid, 4S cembranoid or cembranoid analogue is administered orally, intramuscularly, intravenously or intra-arterially.

In another embodiment, the 4R cembranoid, 4S cembranoid or cembranoid analogue is administered orally in the dose range of 0.5-5 mg/kg body weight for chronic treatment of the neurodamage.

In another embodiment, the 4R cembranoid, 4S cembranoid or cembranoid analogue is administered intramuscularly in the dose range of 0.1-0.5 mg/kg body weight for acute treatment of neurodamage.

In another embodiment, the 4R cembranoid, 4S cembranoid or cembranoid analogue is administered via cerebral artery in the dose range of 5-50 µg/kg body weight or intramuscularly in the dose range of 0.1-0.5 mg/kg body weight for acute treatment of neurodamage.

In another embodiment, the 4R cembranoid, 4S cembranoid or cembranoid analogue is administered with another neuroprotective agent selected from the group consisting of atropine, pralidoxime and midazolam.

In another embodiment, the 4R cembranoid, 4S cembranoid or cembranoid analogue is administered with atropine.

In another embodiment, the 4R cembranoid, 4S cembranoid or cembranoid analogue is administered with atropine in the dose range of 1-10 mg/kg body weight.

Another aspect of the present invention relates to a method for treating OP-induced neuronal damage in a subject. The method comprises administering to the subject an effective amount of 4R cembranoid, 4S cembranoid or a cembranoid analogue.

In one embodiment, the 4R cembranoid, 4S cembranoid or cembranoid analogue is administered orally in the dose range of 0.5-5 mg/kg body weight.

Another aspect of the present invention relates to a neuroprotective pharmaceutical composition. The pharmaceutical composition comprises 4R 4R cembranoid, 4S cembranoid or a cembranoid analogue and a pharmaceutically acceptable carrier.

Another aspect of the present invention relates to a kit for protecting a subject from OP-induced neurodamage. The kit comprises 4R cembranoid, 4S cembranoid or a cembranoid analogue in a container and an instruction on how to use the 4R cembranoid, 4S cembranoid or cembranoid analogue.

In one embodiment, the 4R cembranoid, 4S cembranoid or cembranoid analogue is formulated in a ready-to-dispense form.

In another embodiment, the 4R cembranoid, 4S cembranoid or cembranoid analogue is formulated in a ready-to-dispense single-dose form.

In another embodiment, the kit further contains another neuroprotective agent.

In a related embodiment, the neuroprotective agent is atropine.

In another embodiment, the kit further contains a dispenser for administering the 4R cembranoid, 4S cembranoid or cembranoid analogue.

BRIEF DESCRIPTION OF DRAWINGS

The file of this patent contains at least one drawing executed in color. Copies of this patent with color drawings will be provided by the Patent and Trademark Office upon request and payment of the necessary fee.

FIG. 10A: Representative brain slices from each group. FIG. 10B: Quantification of neuronal degeneration. The graph represents the average score for neurodegeneration in five brain areas. FIG. 10C: Quantification of astrocytes activation. The extent of astrocytes activation was measured in slices stained with nestin antibody using the same method described in FIG. 10B. 4R decreased astrocyte activation in all four areas shown here.

DETAILED DESCRIPTION

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

One aspect of the present invention provides for both prophylactic and therapeutic methods for protecting or treating a subject at risk of, susceptible to or suffering from OP-induced neuronal damage and neurodamages caused by glutamatergic agonists, such as domoic acid found in contaminated shell fish.

In one aspect, the invention provides a method for protecting a subject from OP-induced neuronal damage. The method comprises administering to a subject, prior to or immediately after, the exposure to OP, an effective amount of 4R cembranoid, 4S cembranoid or cembranoid analogue.

Another aspect of the invention pertains to methods for treating OP-induced neuronal damage in a subject. The method comprises administering to a subject with OP-induced neuronal damage an effective amount of 4R cembranoid, 4S cembranoid or cembranoid analogue.

Figure 1:
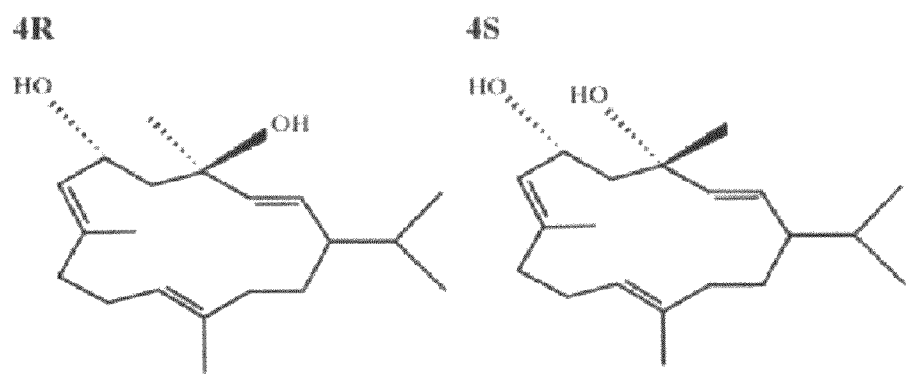
FIG. 1 shows the chemical formula of (1S,2E,4R,6R,7E,11E)-cembra-2,7,11-triene-4,6-diol (4R cembranoid) and (1S,2E,4S,6R,7E,11E)-cembra-2,7,11-triene-4,6-diol (4S cembranoid).

Cembranoids are cyclic diterpenoids found at relatively high concentrations in various tobacco species (approx. 0.2% of the green tobacco leaf) (El Sayed K A, et al. (2007) *Expert Opin Investig Drugs* 16:877-887) as well as in soft corals and other terrestrial plants. FIG. 1 shows the structures of (1S,2E,4R,6R,7E,11E)-cembra-2,7,11-triene-4,6-diol (4R cembranoid) and (1S,2E,4S,6R,7E,11E)-cembra-2,7,11-triene-4,6-diol (4S cembranoid).

Cembranoids are noncompetitive antagonists of nicotinic acetylcholine receptors (nAChR). The 4R cembranoid from tobacco (FIG. 1) is a subtype selective antagonist of the α7 neuronal nAChR with little activity at the α3β4 or the α3β4 subtypes. 4S cembranoid is a stereoisomer of 4R cembranoid and has properties similar to 4R cembranoid. As used herein, the term "cembranoid analogue" refers to synthetic analogues of 4R or 4S cembranoid that have properties similar to 4R or 4S cembranoid.

In one embodiment, the 4R cembranoid or 4S cembranoid is a naturally produced 4R cembranoid or 4S cembranoid. In another embodiment, the 4R cembranoid or 4S cembranoid is a 4R cembranoid or 4S cembranoid isolated from tobacco.

The 4R cembranoid, 4S cembranoid or cembranoid analogue can be administered through a variety of routes. In one embodiment, the 4R cembranoid, 4S cembranoid or cembranoid analogue is administered intravenously. In another embodiment, the 4R cembranoid, 4S cembranoid or cembranoid analogue is administered intra-arterially. In another embodiment, the 4R cembranoid, 4S cembranoid or cembranoid analogue is administered intrathecally. In another embodiment, the 4R cembranoid, 4S cembranoid or cembranoid analogue is administered intramuscularly. In yet another embodiment, the 4R cembranoid, 4S cembranoid or cembranoid analogue is administered orally. Other routes of administration, such as subcutaneous and intraperitoneal administration, may also be employed. For acute treatment, the preferred route is intramuscular injection. For chronic treatment, the preferred route is oral administration.

In prophylactic treatment, 4R cembranoid, 4S cembranoid or cembranoid analogue is administered orally in a dose range of 0.5-5 mg/kg body weight 1-2 hours before exposure. After exposure, 4R cembranoid, 4S cembranoid or cembranoid analogue is administered intramuscularly in a dose range of 0.1-0.5 mg/kg body weight up to several hours post-exposure. For existing neurodamage, 4R cembranoid, 4S cembranoid or cembranoid analogue is administered orally in a dose range of 0.5-5 mg/kg body weight. In one embodiment, 4R cembranoid, 4S cembranoid or cembranoid analogue is administered orally in the dose range of 0.5-5 mg/kg body weight for chronic treatment of neurodamage. In another embodiment, 4R cembranoid, 4S cembranoid or cembranoid analogue is administered intramuscularly in the dose range of 0.1-0.5 mg/kg body weight for acute treatment of neurodamage. In another embodiment, 4R cembranoid, 4S cembranoid or cembranoid analogue is administered via cerebral artery in the dose range of 5-50 μg/kg body weight. In yet another embodiment, 4R cembranoid, 4S cembranoid or cembranoid analogue is administered intramuscularly in the dose range of 0.1-0.5 mg/kg body weight for acute treatment of the neurodamage.

In another embodiment, 4R cembranoid, 4S cembranoid or cembranoid analogue is administered in a dose range of 0.002-0.02 mg/kg body weight/day. In one embodiment, the 4R cembranoid, 4S cembranoid or cembranoid analogue is administered in a dose range of 0.02-0.5 mg/kg body weight/day. In another embodiment, the 4R cembranoid, 4S cembranoid or cembranoid analogue is administered in a dose range of 0.5-1.0 mg/kg body weight/day. In yet another embodiment, the 4R cembranoid, 4S cembranoid or cembranoid analogue is administered in a dose range of 1.0-10 mg/kg body weight/day.

In one embodiment, the neuronal injury is brain injury. In another embodiment, the neuronal injury is OP-induced brain injury.

Administration with other Neuroprotective Agent

In certain embodiments, 4R cembranoid, 4S cembranoid or cembranoid analogue is co-administered with another neuroprotective agent. Examples of such neuroprotective agent include, but are not limited to, atropine, pralidoxime and midazolam.

In one embodiment, 4R cembranoid, 4S cembranoid or cembranoid analogue is co-administered with atropine. In another embodiment, 4R cembranoid, 4S cembranoid or cembranoid analogue is co-administered with atropine in a dose range of 1-10 mg atropine/kg body weight.

Determination of Toxicity

Toxicity and therapeutic efficacy of 4R cembranoid, 4S cembranoid or cembranoid analogue can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, to reduce side effects.

The data obtained from the cell culture assays and animal studies can be used in formulating a range of dosage for use in humans. The dosage lies preferably within a range of circulating concentrations that includes the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmacogenomics

With regard to both prophylactic and therapeutic methods of treatment, such treatments may be specifically tailored or modified, based on knowledge obtained from the field of phaunacogenomics. The "Pharmacogenomics," as used herein, includes the application of genomics technologies such as gene sequencing, statistical genetics, and gene expression analysis to drugs in clinical development and on the market. More specifically, the term refers the study of how a subject's genes determine his or her response to a drug (e.g., a subject's "drug response phenotype" or "drug response genotype"). Thus, another aspect of the invention provides methods for tailoring an individual's prophylactic or therapeutic treatment with 4R cembranoid according to that individual's drug response. Pharmacogenomics allows a clinician or physician to target prophylactic or therapeutic treatments to subjects who will most benefit from the treatment and to avoid treatment of subjects who will experience toxic drug-related side effects.

In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is hemolysis after ingestion of oxidant drugs (anti-malarials, sulfonamides, analgesics, nitrofurans) and consumption of fava beans.

One pharmacogenomic approach to identifying genes that predict drug response, known as "a genome-wide association," relies primarily on a high-resolution map of the human genome consisting of already known gene-related sites (e.g., a "bi-allelic" gene marker map which consists of 60,000-100, 000 polymorphic or variable sites on the human genome, each of which has two variants). Such a high-resolution genetic map can be compared to a map of the genome of each of a statistically substantial number of subjects taking part in a Phase II/III drug trial to identify genes associated with a particular observed drug response or side effect. Alternatively, such a high resolution map can be generated from a combination of some ten-million known single nucleotide polymorphisms (SNPs) in the human genome. As used herein, an "SNP" is a common alteration that occurs in a single nucleotide base in a stretch of DNA. For example, an SNP may occur once per every 1,000 bases of DNA. An SNP may be involved in a disease process. However, the vast majority of SNPs may not be disease associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals. Thus, mapping of the SRGs of the invention to SNP maps of schizophrenia patients may allow easier identification of these genes according to the genetic methods described herein.

Alternatively, a method termed the "candidate gene approach," can be utilized to identify genes that predict drug response. According to this method, if a gene that encodes a drug target is known, all common variants of that gene can be fairly easily identified in the population and it can be detei mined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyl-transferase 2 (NAT 2) and cytochrome P450 enzymes CYP2D6 and CYPZC19) has provided an explanation as to why some subjects do not obtain the expected drug effects or show exaggerated drug response and serious toxicity after taking the standard and safe dose of a drug. These polymorphisms are expressed in two phenotypes in the population, the extensive metabolizer and poor metabolizer. The prevalence of poor metabolizer phenotypes is different among different populations. For example, the gene coding for CYP2D6 is highly polymorphic and several mutations have been identified in poor metabolizers, which all lead to the absence of functional CYP2D6. Poor metabolizers of CYP2D6 and CYP2C19 quite frequently experience exaggerated drug response and side effects when they receive standard doses. If a metabolite is the active therapeutic moiety, poor metabolizers show no therapeutic response, as demonstrated for the analgesic effect of codeine mediated by its CYP2D6-formed metabolite morphine. The other extreme are the so called "ultra-rapid metabolizers" who do not respond to standard doses. Recently, the molecular basis of ultra-rapid metabolism has been identified to be due to CYP2D6 gene amplification.

Alternatively, a method termed the "gene expression profiling" can be utilized to identify genes that predict drug response. For example, the gene expression of an animal dosed with a drug can give an indication whether gene pathways related to toxicity have been turned on.

Information generated from more than one of the above pharmacogenomic approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with 4R cembranoid, 4S cembranoid or cembranoid analogue.

Pharmaceutical Compositions

Another aspect of the present invention is further directed to pharmaceutical compositions comprising 4R cembranoid, 4S cembranoid or cembranoid analogue and a pharmaceutically acceptable carrier. As used herein the language "pharmaceutically acceptable carrier" is intended to include any and all solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions.

A pharmaceutical composition of the invention is formulated to be compatible with its intended route of administration. Examples of routes of administration include parenteral, e.g., intravenous, intraarterial, intrathecal, intradermal, subcutaneous, oral, transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the requited particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the 4R cembranoid in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above, In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the bioactive compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the therapeutic moieties, which may contain a bioactive compound, are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from e.g. Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art.

It is especially advantageous to formulate oral or parenteral compositions in dosage unit form for ease of administration and uniformity of dosage. Dosage unit form, as used herein, includes physically discrete units suited as unitary dosages for the subject to be treated; each unit contains a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

In another embodiment, the pharmaceutical composition further comprises another neuroprotective agent. Examples of such neuroprotective agent include, but are not limited to, atropine, pralidoxime and midazolam.

In one embodiment, the pharmaceutical composition further comprises atropine.

Kits

The invention also encompasses kits for treating a subject at risk of, susceptible to or suffering from OP-induced neuronal damage. The kit comprising 4R cembranoid, 4S cembranoid or cembranoid analogue packaged in a suitable container and instructions for using the kit. In one embodiment, the 4R cembranoid, 4S cembranoid or cembranoid analogue is formulated in a ready-to-dispense form. In one embodiment, the 4R cembranoid, 4S cembranoid or cembranoid analogue is packaged in single dosage form. In another embodiment, the kit further contains another neuroprotective agent, such as atropine. In another embodiment, the kit further contains a dispenser, such as a syringe or an inhaler, for administering 4R cembranoid, 4S cembranoid or cembranoid analogue.

In one embodiment, the neuronal injury is brain injury.

The present invention is further illustrated by the following examples which should not be construed as limiting. The contents of all references, patents and published patent applications cited throughout this application, as well as the Figures and Tables are incorporated herein by reference.

EXAMPLE 1

The Hippocampal Slice as a Model for Determination of Neuotoxicity and Neuroprotection Acute hippocampal slices are a choice preparation to study the early synaptic excitotoxic and neuroprotective events. In acute slices, most of the circuitry of the original tissue is preserved, the ratio of interneurons to pyramidal neurons is unchanged, and there is no evidence of major alterations in receptor activity. Stimulation of afferents allows measuring synaptically-elicited population spikes (PSs) from about 30 to 60 pyramidal neurons.

The use of PSs to assess the degree of damage has the advantage that the size of the PS is directly proportional to the number of functionally active pyramidal neurons (Andersen P, et al., *Exp Brain Res* 13:208-221). In addition, this preparation is well suited to study the early functional neuronal damage before the onset of cell death. Drugs can be easily administered, and the electric activity can be monitored. However, the acute slice shows a considerable rundown after more than 8-10 hours. For this reason, only a few studies have addressed delayed cell death in acute slices (Wallis R A, et al. (1995) *Brain Res* 674:75-81; Wang T, et al. (1999) *Stroke* 30:2400-2407). The comparison of the early effect of experimental ischemia on the electric activity in acute slices with delayed neuronal death in cultured slices was consistent with the concept that both, electric activity and death, represent the same event in a different time scale (Small D L, et al. (1997) *Brain Res* 753:209-218).

1-1A. Slice Preparation and Electrophysiological Recordings

The methods for the dissection of hippocampi and the preparation of slices have been previously described (Ferchmin P A, et al. (2003) *J Pharmacol Exp Ther* 305:1071-1078). Briefly, hippocampi were dissected over ice; transversal 400 µm thick slices were cut with a manual slicer and immediately transferred to an incubation chamber. The chamber consisted of a temperature-controlled bath surrounding an acrylic plate covered with nylon mesh; the plate is divided into three lanes with independent perfusion. For dissection and incubation, a standard artificial cerebrospinal fluid (ACSF) saturated with 95% $O_2$, 5% $CO_2$ was used, containing (in mM): 125 NaCl, 3.3 KCl, 1.25 $NaH_2PO_4$, 2 $MgSO_4$, 2 $CaCl_2$, 25 $NaHCO_3$, and 10 glucose. The slices were kept in the lanes over the mesh, at the interface between ACSF and warmed and humidified 95% $O_2$, 5% CO2 at 34±1° C. A bipolar electrode placed in the stratum radiatum was used to stimulate the Shaffer collateral incoming fibers with a constant current for 0.2 ms. The resulting population spike (PS) was recorded in stratum pyramidale with a glass electrode filled with 2 M NaCl, with impedance of 1 to 5 MΩ. Twenty seven slices from the hippocampi of two rats were distributed equally among the three lanes of the incubation chamber and incubated for one hour in ACSF to allow the slices to recover from the trauma of the dissection. One hour after dissection, the minimum stimulus needed to elicit a threshold PS was determined. Then each slice was stimulated with a stimulus twice the strength required to elicit a threshold PS. This initial response was recorded as PS area (ms×my) and compared with the final response elicited by the same stimulus strength recorded from the same position after the experimental treatment was finished and the slices were washed out for 1 hour with normal ACSF to eliminate lingering drug effects. The percentage of the initial response remaining at the end of the experiment is used as a measure of electrophysiological recovery.

1-2A. Minimal Neurotoxicity Tests.

Minimal neurotoxicity induced by each compound was detected in mice using the standardized Rotarod test (Dunham N W, et al. (1957) *J Am Pharm Assoc Am Pharm Assoc (Baltim)* 46:208-209). Untreated control mice, when placed on a 6 r.p.m. rotation rod, can maintain their equilibrium for a prolonged period of time. Neurological impairment can be demonstrated by the inability of mice to maintain equilibrium for one minute in each of three successive trials (Stables J P, et al. (1997) *Co. Ltd Eurotext*, Ch 16, pp 191-198. ISBN 086196554X). Each compound was tested at i.p. doses of 30, 100, and 300 mg/kg, at 0.5 and 4 hours after the injection. Rats were examined for behavioral toxicity by the positional sense test and a gait and stance test (Supra). 4R was administered orally at 30 mg/Kg, and the observations were done at 0.25, 0.5, 1.0, 2.0 and 4.0 hours after administration.

EXAMPLE 2

Paraoxon Decreases the Area of PSS in the Acute Hippocampal Slice

Figure 2:
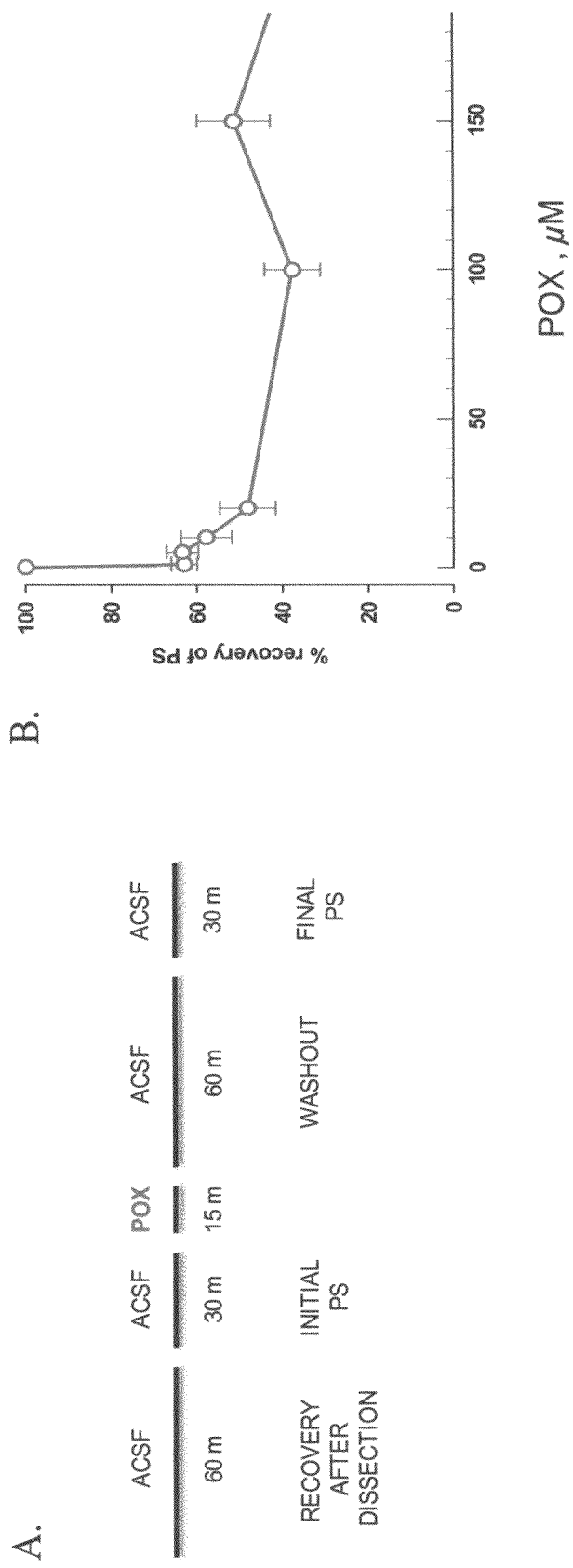
FIG. 2 is a composite of diagrams showing the experimental protocol used to determine the effect of POX on the population spike (PS) area (FIG. 2A) and the concentration curve for POX inhibition of PS (FIG. 2B, seven or more slices per point). Abbreviations:ACSF, artificial cerebrospinal fluid; PS, population spike; POX, paraoxon.

FIG. 2A illustrates the experimental protocol used to determine the effect of POX on the PSs recorded from the CA1 area of the rat hippocampal slice. At 1 µM, POX decreased the PS area to 60% of control value. Additional experiments demonstrated that the severity of the damage did not increase by lengthening the time of exposure from 15 to 20 and 30 min (data not shown).

POX concentration curve is shown in FIG. 2B. The slice was incubated with 0 µM (control) to 200 µM POX for 15 m following the protocol in FIG. 2A. Maximum inhibition of the PS was close to 50%; the remaining 50% of the PS area was resistant to POX up to the maximum concentration of 200 µM. POX IC50 was close to 1 µM.

EXAMPLE 3

4R Cembranoid Relieves the Neurotoxic Effect of POX

Figure 3:
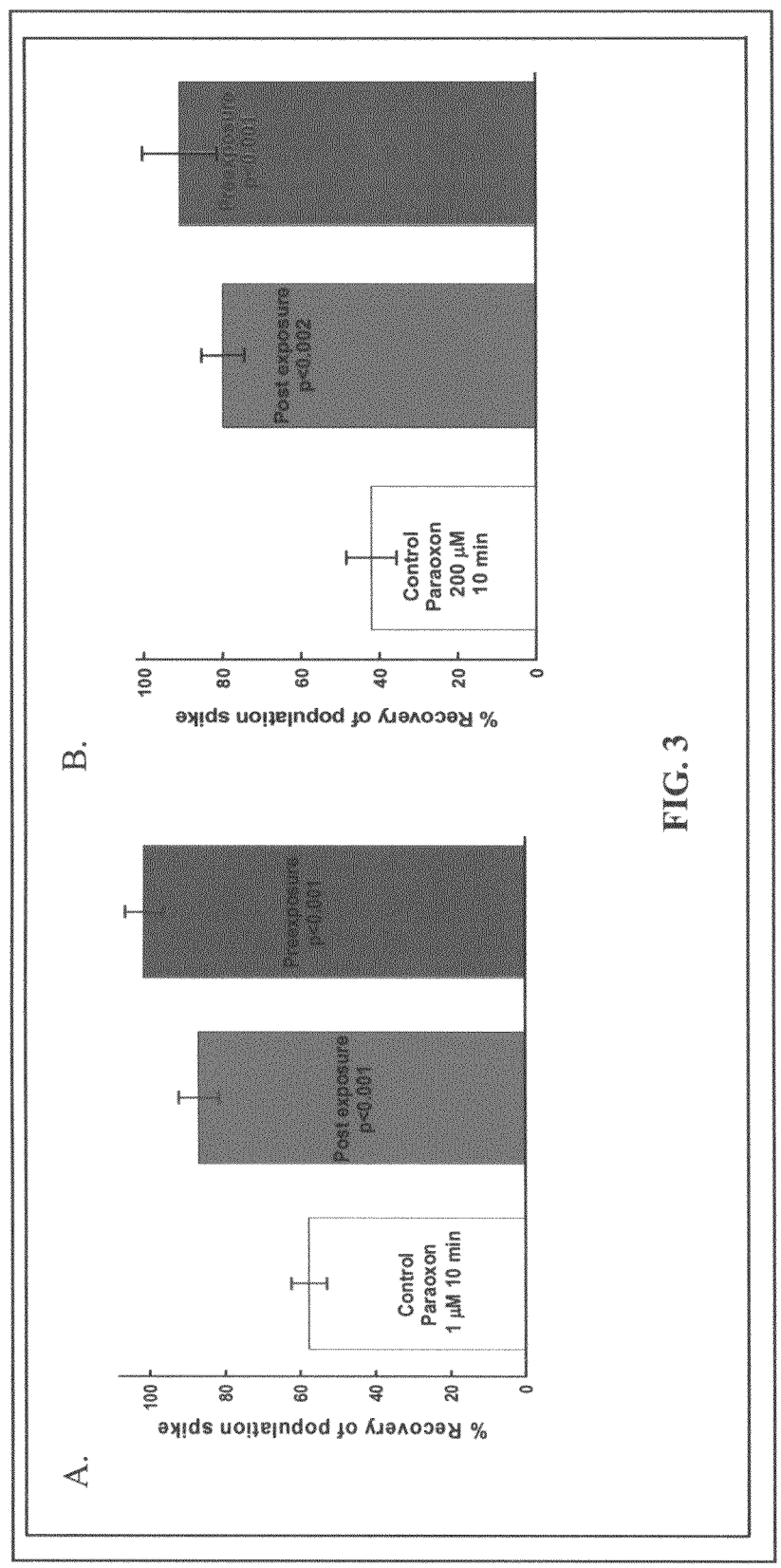
FIG. 3 is a composite of diagrams showing that post or pre-treatment with 2 µm 4R cembranoid protects the PS against 1 µM POX (FIG. 3A, N=21 slices per group) and 200 µM POX ((FIG. 3B, N=14 slices per group).

FIG. 3A illustrates the effect of 1 µM POX on the PS and its reversal by 2 µM 4R cembranoid. 4R cembranoid was applied to the slice for one hour either before or immediately after POX. In this experiment, 1 µM POX alone decreased the PS to just under 60% of control value. When 2 µM 4R cembranoid was applied before POX, close to 100% recovery was obtained; while over 80% recovery was obtained with 4R cembranoid applied immediately after POX.

FIG. 3B shows a similar experiment performed with 200 µM POX, which decreased the PS to almost 40% of control value. 90% recovery was obtained when 2 µM 4R cembranoid was applied before POX and 80% recovery was obtained with 4R cembranoid applied immediately after POX.

These results show that 2 µM 4R cembranoid provided almost complete protection from POX whether applied before or immediately after a large excess of POX.

EXAMPLE 4

Figure 4:
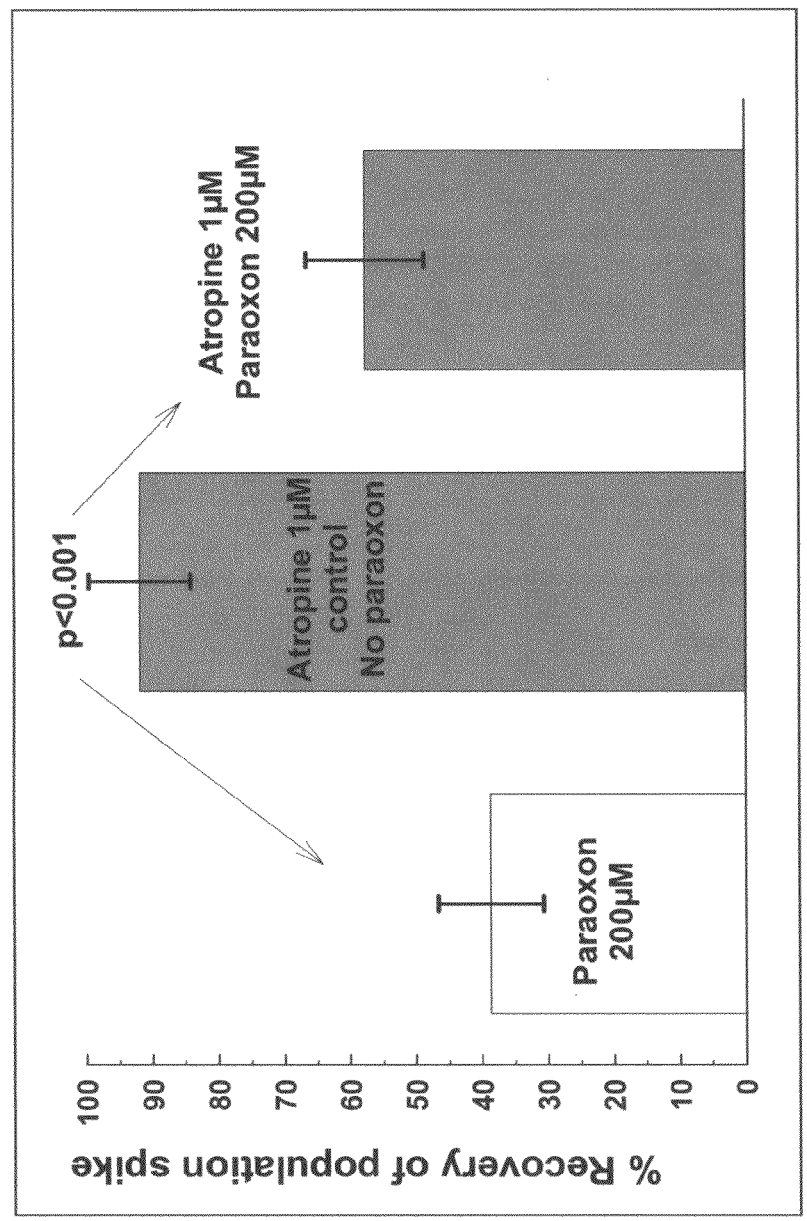
FIG. 4 is a diagram showing that atropine is neither harmful to the slice nor is it neuroprotective against 200 µM POX (N=14 slices per group).
Figure 5:
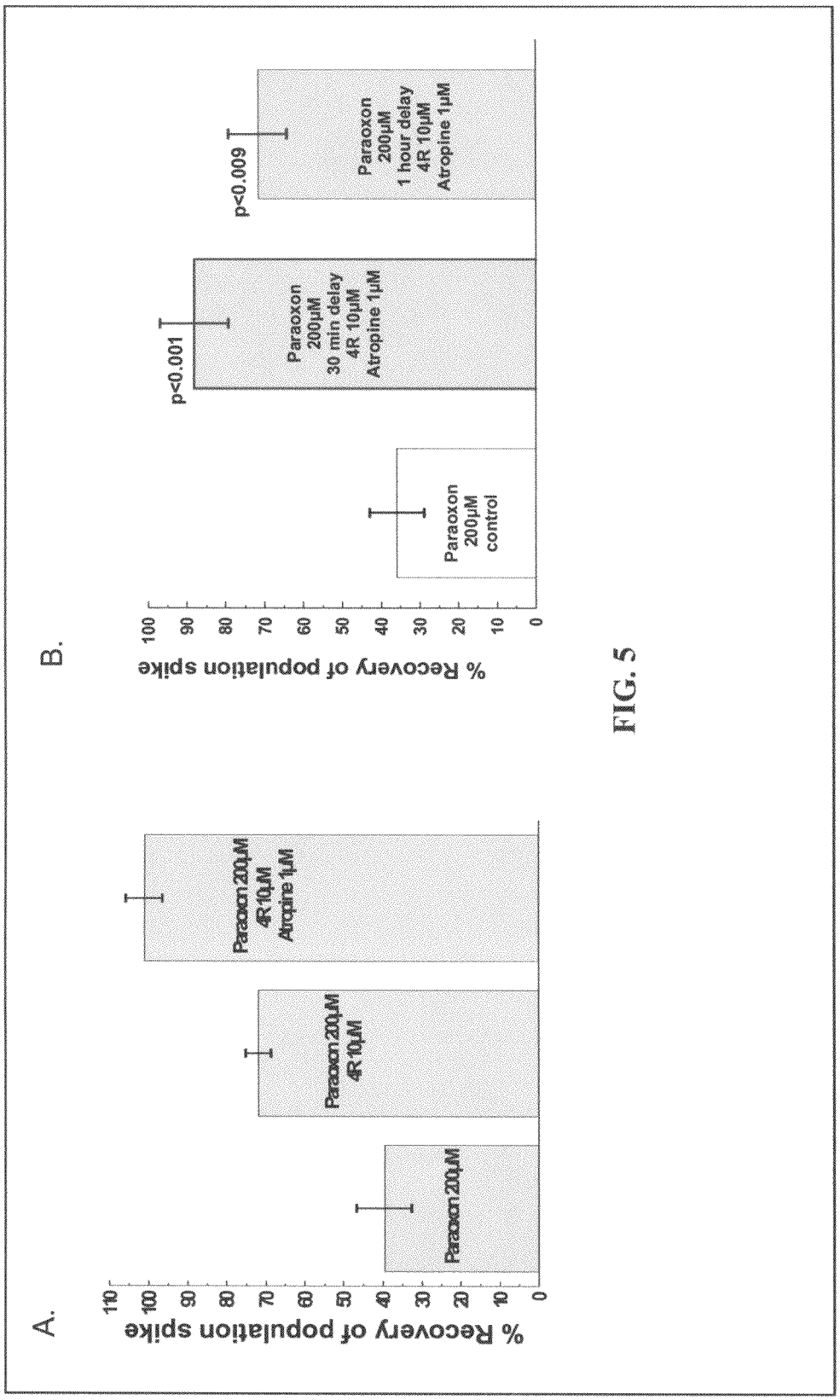
FIG. 5 is a composite of diagrams showing that the neuroprotective effect of 4R cembranoid is enhanced in the presence of atropine (FIG. 5A, all experimental groups were significantly different from each other, N=21 slices per group, p<0.0001), and the protection is effective up to one hour after exposure to POX (FIG. 5B, the two experimental groups are significantly different from control. N=7 slices per group).

4R Cembranoid in Combination with Atropine Protects with a Long Window of Therapeutic Opportunity Atropine is the most frequently used antidote for OPs poisoning in vivo. The following experiments were designed to test whether atropine is toxic to the slice and whether it can relieve POX-inflicted damage. The results presented in FIG. 4 indicate that incubating the slice for 1 hour with 1 µM atropine did not affect PS area. In addition, preincubation with atropine for 1 hour before POX did not enhance the recovery of PSs. Thus under the tested conditions, atropine is neither harmful to the slice nor is it neuroprotective against 200 µM POX. Next, the effect of 4R cembranoid and atropine combinations was tested. FIG. 5A shows that application of 10 µM 4R cembranoid 15 min after 200 µM POX increased PS area from 40% of control to 70% of control. However, when 10 µM 4R cembranoid was applied in combination with 1 µM atropine, 100% protection was achieved. Therefore, a combination of 4R cembranoid and atropine was more effective in protecting the slice from POX than 4R alone.

The same combination of 4R cembranoid and atropine was also applied 30 or 60 min after washing out the POX. FIG. 5B shows the promising result that this combination offers significant protection after a 30 min (90%) and even after a 1 hour delay (70%).

EXAMPLE 5

4R Cembranoid Displays Only Minimal Neurotoxicity in Rats and Mice 4R cembranoid and its isomer 4S cembranoid were tested for neurotoxicity by the Anticonvulsant Screening Program (ASP) at the National Institute of Neurological Disorders and Stroke (NINDS). The test results are shown in Table 1. All results are reported as the ratio of the number of animals failing the test over the number tested at a given time point and dose. The only suspected toxicity was found 0.5 hours after i.p. injection of the enormous dose of 300 mg/kg of 4R cembranoid. The suspected toxicity was reflected in 1 mouse out of 4 falling from the rod. 4S showed more toxicity with 1 mouse out of 8 failing at the dose of 100 mg/kg and 3 of 4 failing at 300 mg and 0.5 h after injection. There was no toxicity of 30 mg/kg of 4R cembranoid administered orally to rats from 15 min to 4 hours later. None of the 4 rats failed the positional sense test or the gait and stance test, up to 4 h after oral administration of 30 mg/kg 4R.

The results demonstrated that (1) 4R cembranoid was non-toxic in mice at least up to an i.p. dose of 100 mg/kg and possibly up to 300 mg/kg, (2) 4R cembranoid was non-toxic in rats at 30 mg/kg (oral), and (3) 4S cembranoid was somewhat more toxic than 4R cembranoid in mice.

TABLE 1

4R cembranoid and 4S cembranoid toxicity in mice

| 4R toxicity in mice | | 4S toxicity in mice | |
|---|---|---|---|
| Dose | Time after injection | Dose | Time after injection |
| (mg/kg) | 0.5 h | 4.0 h | (mg/kg) | 0.5 h | 4.0 h |
| 30 | 0/4 | 0/2 | 30 | 0/4 | 0/2 |
| 100 | 0/8 | 0/4 | 100 | 1/8 | 0/4 |
| 300 | 1/4 | 0/2 | 300 | 3/4 | 1/2 |

EXAMPLE 6

Figure 6:
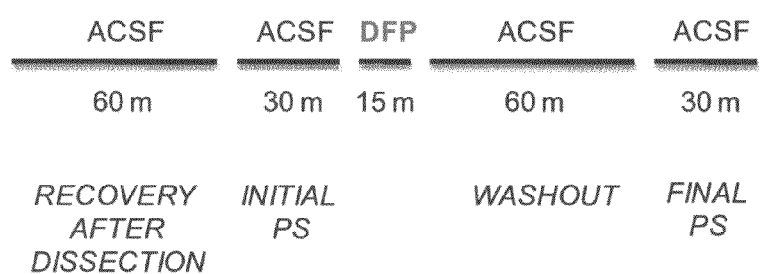
FIG. 6 is a composite of diagrams showing diisopropylfluorophosphate (DFP) decreases the area of the population spike (PS) in a concentration-dependent manner. Panel A is the experimental protocol used to determine the effect of DFP on the PS. Abbreviations: ACSF, artificial cerebrospinal fluid; PS, population spike. Panel B is the concentration curve for DFP inhibition of PS. N=7 or more slices per point.
Figure 6:
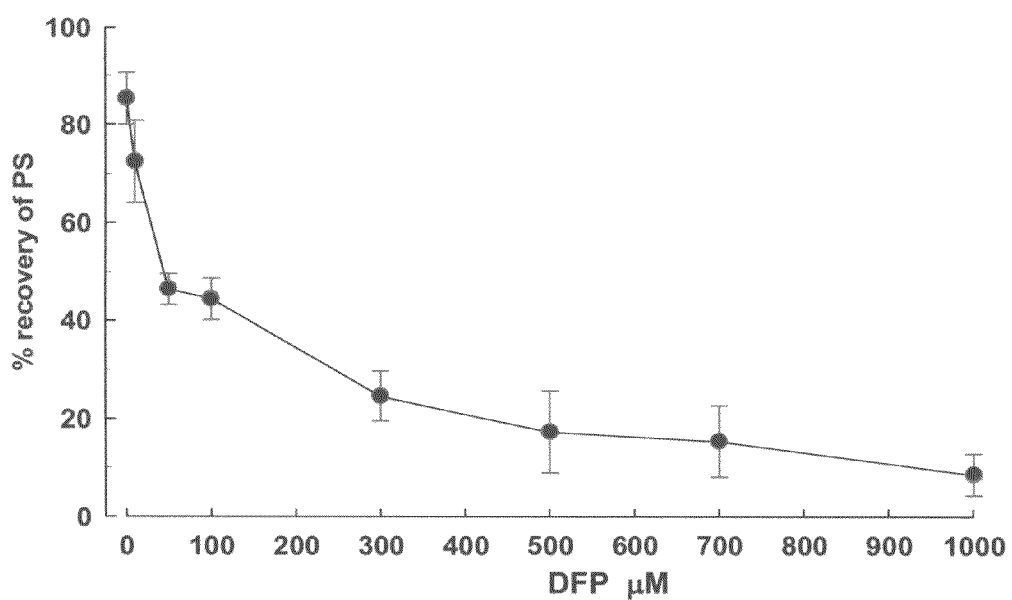

Diisopropylfluorphosphate (DFP) Decreases the Area of Population Spikes (PS) in the Acute Hippocampal Slice FIG. 6A illustrates the experimental protocol used to determine the effect of DFP on the PS recorded from the CA1 area of the rat hippocampal slice. Initial experiments demonstrated that the severity of damage did not increased by lengthening the exposure from 10 to 30 min (data not shown).

FIG. 6B shows the dose-related DFP inhibition of PS. The slice was incubated with 0 µM (control) to 1000 µM DFP for 10 min following the protocol in FIG. 6A. 1 mM DFP produced close to total inhibition of the PS; DFP $IC_{50}$ was close to 40 µM.

EXAMPLE 7

4R Cembranoid Relieves the Neurotoxic Effect of DFP

Figure 7:
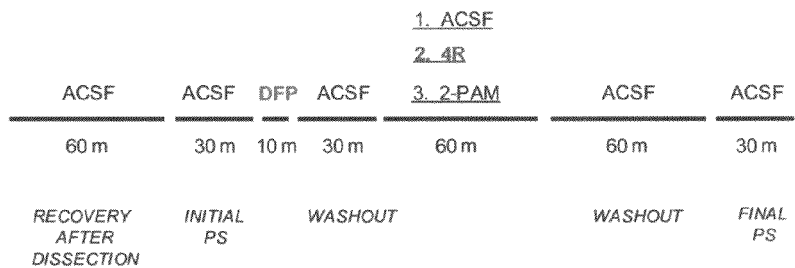
FIG. 7 is a composite of diagrams showing 4R protects the PS from DFP-inflicted damage. Panel A is the experimental protocol. Panel B shows that 10 µM 4R increases the PS recovery after treatment with 100 µM DFP. Panel C shows that 4R is more efficacious than pralidoxime (2-PAM) in promoting PS recovery after treatment with 100 µM DFP. There were 14 slices in each experimental condition.
Figure 7:
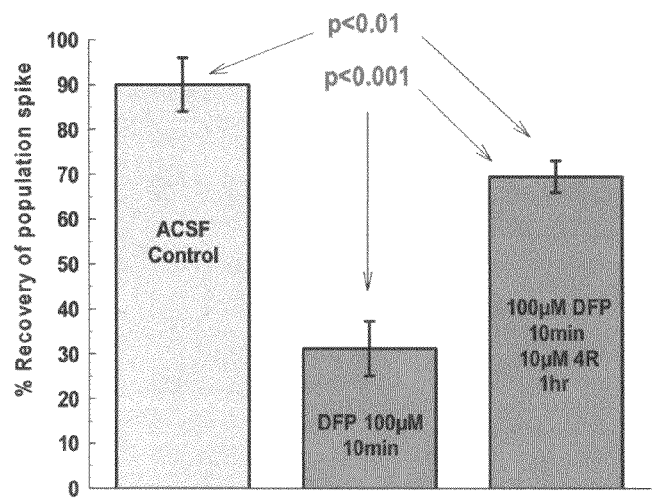
Figure 7:
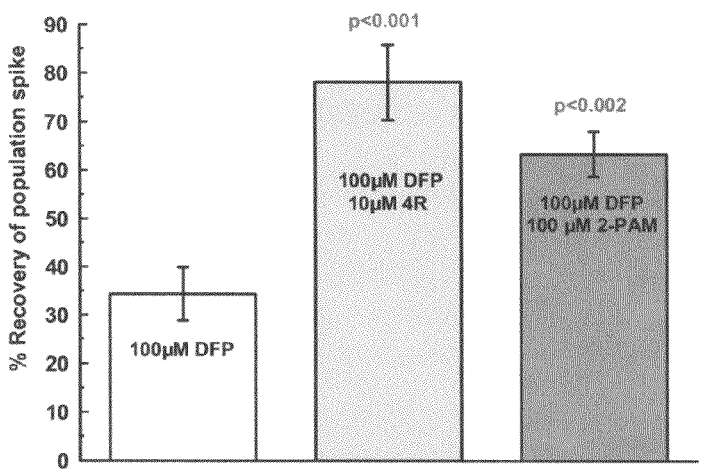

FIGS. 7A to 7C illustrate the effect of 100 µM DFP on the PS and its reversal by 10 µM 4R cembranoid. 4R cembranoid was applied to the slice 30 mM after DFP (FIG. 7A). In these experiments, 100 µM DFP alone decreased the PS to 30%-35% of control value. When 10 µM 4R cembranoid was applied, 70%-80% recovery was obtained (FIGS. 7B and 7C). By comparison, about 65% recovery was obtained with the classical antidote pralidoxime (2-PAM) at 100 µM concentration (FIG. 7C).

These results show that 10 µM 4R cembranoid provided almost complete protection from DFP when applied 30 min after a large excess of DFP.

EXAMPLE 8

4R Cembranoid in Combination with Atropine Protects Against DFP

Figure 8:
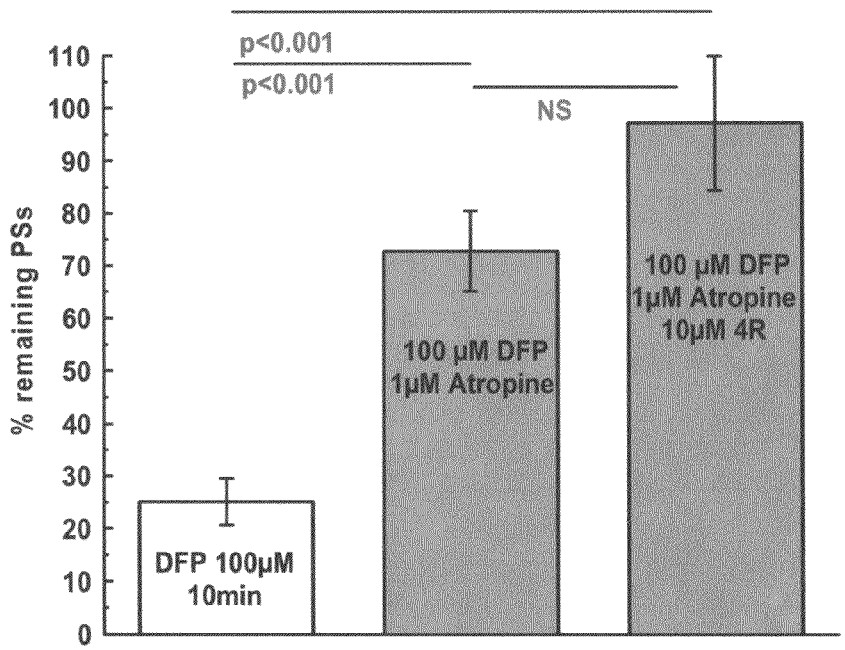
FIG. 8 is a diagram showing that atropine alone or in combination with 4R protects the PS against DFP-inflicted damage. Significance is shown in the figure. There were 14 slices in each experimental condition.

Atropine is the most frequently used antidote for OPs poisoning in vivo. Results discussed in Example 4 indicated that, under our conditions, atropine is not harmful to the slice. The following experiments were designed to test whether atropine can relieve DFP-inflicted damage. The results presented in FIG. 8 indicate that 10 min of superfusion with 100 µM DFP decreased the PS recovery to 25±4.4%, 1 µM atropine applied 30 min after DFP significantly increased the recovery to 72.8±1.7% and the combination of 4R and atropine increased the recovery to 97.1±12.8%.

These results suggest that, under the tested conditions, 1 uM atropine is per se neuroprotective against 100 uM DFP and a combination of 4R cembranoid and atropine is also effective in protecting the slice from DFP.

EXAMPLE 9

In Vivo Protocol for the Study of Protection from DFP-Inflicted Neuropathotology In order to study long-lasting OP-inflicted neuropathology, it is necessary to find a model for OP toxicity in which there is low mortality and significant neuropathology. These requirements are fulfilled by the Pyridostigmine Ipratropium-DFP (PID) model, in which DFP-related mortality is decreased by prior injection of a reversible acetylcholinesterase inhibitor (pyridostigmine) and a muscarinic antagonist (ipratropium). Since neither pyridostigmine nor ipratropium cross the blood-brain barrier, the brain is not protected from DFP-induced neurodegeneration.

Figure 9:
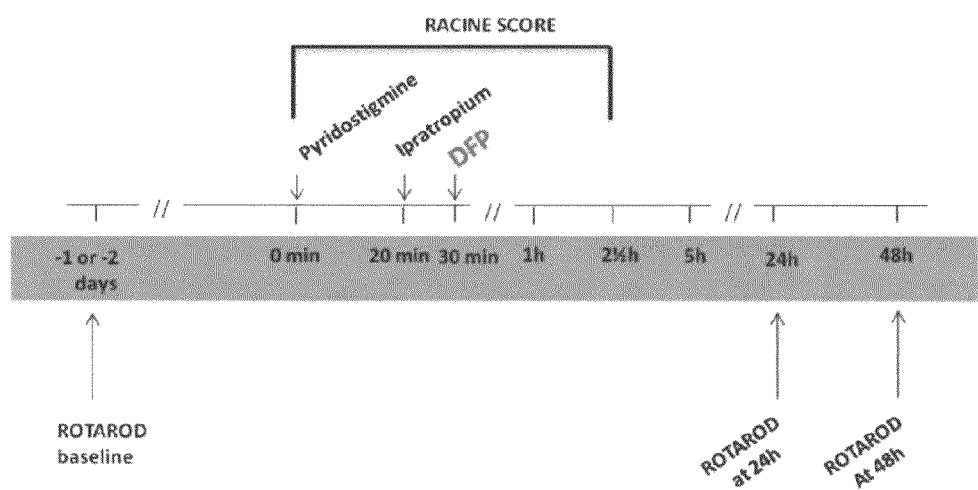
FIG. 9 is the Pyridostigmine-Ipratropium-DFP (PID) model experimental protocol. Rats in the experimental group (PID group) were injected with 0.1 mg/kg (im) pyridostigmine followed 20 min later by 23 mg/kg (im) ipratropium and after another 10 min with 9 mg/kg (ip) DFP. The control group (PIW group) received pyridostigmine, ipratropium and water, while the vehicle control group (SSW group) received saline, saline and water. Using this model, behavior was monitored with a modified Racine scale and the Rotarod test. Finally, the rats were anesthetized, perfused and brain damage was assessed using histological methods. AChE was measured in blood and brain samples.

FIG. 9 illustrates the experimental protocol for the PID model. The rats in the experimental group (PID group) were injected with pyridostigmine (0.1 mg/kg), followed 20 min later by ipratropium (23 mg/kg) and after another 10 min with DFP (9 mg/kg). Control group 1 (PIW group) received pyridostigmine, ipratropium and water while the vehicle control group (SSW group) received saline, saline and water. The effects of these treatments on neuropathology and behavior were assessed at 24 h and 48 h after DFP.

Mortality was 36% in the PID group and none in controls.

Convulsions, measured with the Racine scale, were severe in the PID group while the PIW rats displayed only mild increase in Racine scores.

Rotarod test revealed severe motor deficit 24 h after DFP with partial recovery 48 h after DFP.

Brain ACNE activity was profoundly inhibited at 24 h and 48 h after DFP.

Neuronal degeneration as measured by cresyl violet stain and caspase 3 activation methods was more pronounced in the PID group than in the SSW controls.

In conclusion, the HD model was characterized with behavioral, enzymatic and histological methods, which revealed severe DFP-inflicted damage in rat behavior and brain histology.

EXAMPLE 10

4R Cembranoid Protects the Rat Brain Against DFP In Vivo.

In order to study the effect of 4R cembranoid on DFP-inflicted damage in vivo, sixteen rats were injected following the PID paradigm (see FIG. 9). One hour before injecting DFP, 8 experimental rats were injected with 6 mg/kg (SC) 4R cembranoid and 8 controls with the DMSO vehicle. Six experimental-control pairs were sacrificed 48 hours after DFP and two 24 hours after. Brains were stained with amino cupric silver (ACS) stain that detects disintegrative degeneration (de Olmos et al., 1994) and nestin, a marker of activated astrocytes that appear in response to injury (Douen et al., (2004) *Brain Research* 1008: 139-146).

Figure 10A:
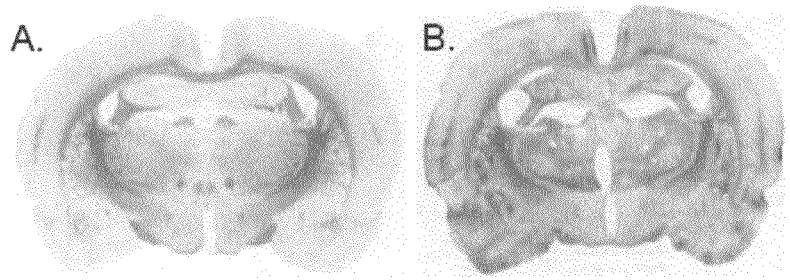
FIGS. 10A-10C show that 4R cembranoid protects the rat brain against DFP damage in vivo. Sixteen rats were injected with DFP following the ND paradigm described in FIG. 9. One hour before injecting DFP, 8 experimental rats were injected with 6 mg/kg (sc) 4R cembranoid and 8 controls with the DMSO vehicle. Six experimental-control pairs were sacrificed 48 hours after DFP and two 24 hours after. Brains were stained with amino cupric silver (ACS) stain that detects disintegrative degeneration and nestin stain, a marker of activated astrocytes that appear in response to injury.
Figure 10A:
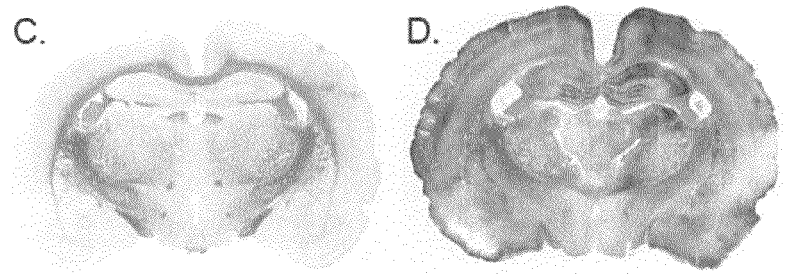
Figure 10A:
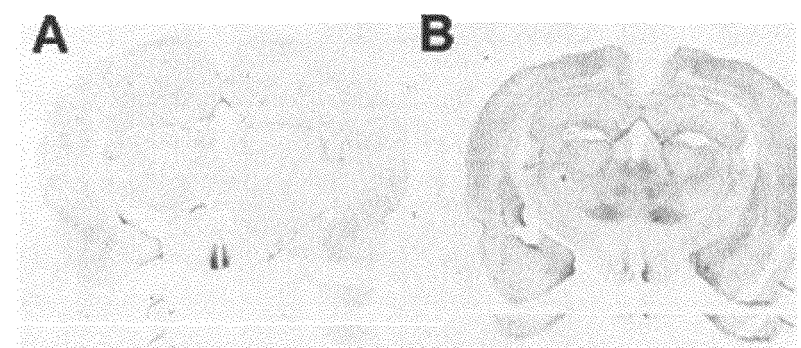
Figure 10A:
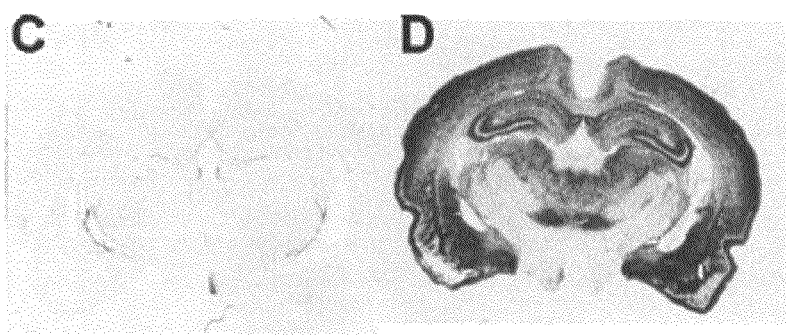
Figure 10B:
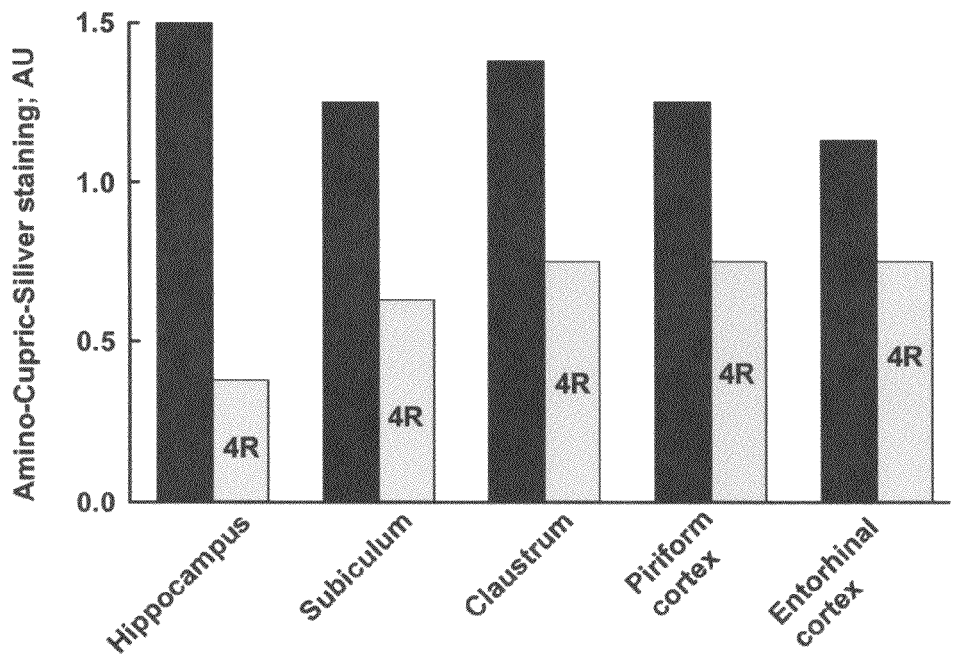
Figure 10C:
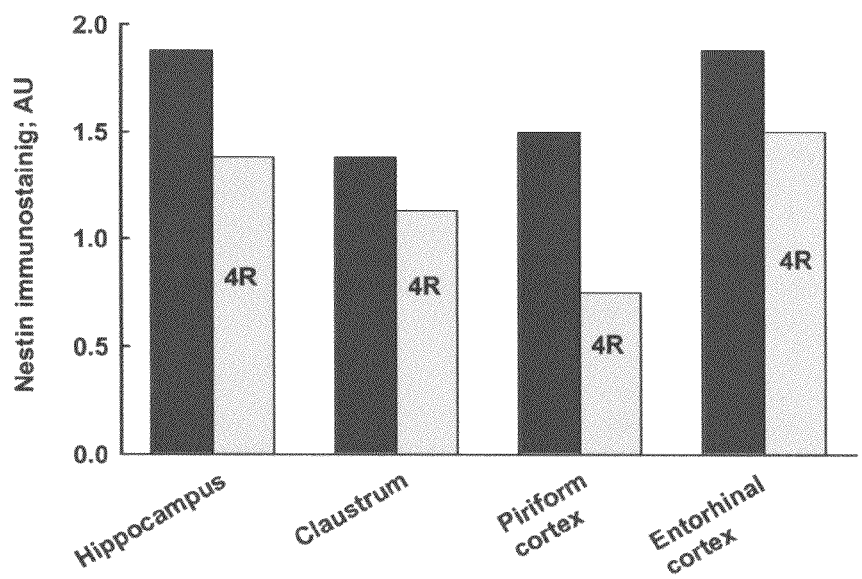

Both the ACS and nestin staining methods indicated that the damage caused by DFP was mitigated by application of 4R (FIGS. 10A-10C). Representative pictures shown in FIG. 10A illustrate a drastic decrease in neuronal degeneration in the brains of rats receiving 4R cembranoid as compared to vehicle control. Similar results were seen with nestin staining, indicating that 4R cembranoid decreased astrocyte activation in response to injury.

The extent of neurodegeneration in the ACS stained slices was scored by three trained lab members that were not aware of the treatment of the subjects. The neurodegeneration was assessed on a scale of 0-5. DMSO controls showed strong neurodegeneration across all areas in 3 out of 8 rats, and the average score per rat (across all areas) was 1.30. 4R injected rats showed milder neurodegeneration across all areas in 2 out of 8 rats; the average score per rat in the 4R group was 0.65. That represents a 49% reduction in neurodegeneration in 4R rats over the vehicle injected controls (FIG. 10B).

The extent of astrocytes activation was measured in slices stained with nestin antibody using the same scoring method described above. As shown in FIG. 10C, Application of 4R cembranoid decreased astrocyte activation in all four areas.

In conclusion, these results indicate that 4R cembranoid produced a large decrease in DFP-inflicted neuropathology.

In summary, 4R cembranoid is a promising neuroprotective compound with activity against a variety of neural insults that include organophosphates, NMDA, and ischemia. The mechanism of neuroprotection of 4R cembranoid is mediated by activation of Ald/PKB and inhibition of neuronal apoptosis.

4R cembranoid is a natural product, which is devoid of obvious toxicity in rats or humans. It does not affect exploratory activity or general behavior in rats (Ferchmin P A, et al. (2001) *J Neurosci Res* 64:18-25). 4R cembranoid has several additional favorable properties. 4R cembranoid inhibits COX-2 and therefore has intrinsic anti-inflammatory activity (Olsson E, et al. (1993) *Planta Med* 59:293-295) which is desirable for a neuroprotective drug. 4R cembranoid readily penetrates into the brain and is promptly metabolized in the liver and excreted as a soluble metabolite. As an antidote against OPs, 4R cembranoid fills in a novel niche that is not targeted by any of the classical antidotal drugs. Thus, 4R cembranoid, as well as 4S cembranoid and cembranoid analogues, could be an excellent addition to the existing pharmacological armamentarium against OPs poisoning.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following embodiments. The embodiments are intended to cover the components and steps in any sequence which is effective to meet the objectives there intended, unless the context specifically indicates the contrary.

What is claimed is:

1. A method for protecting a subject from organophosphate (OP)-induced neuronal injury, comprising:
administering to a subject at risk for exposure to or in need of treatment from said OP-induced neuronal injury a 4R cembranoid, 4S cembranoid or a cembranoid analogue prior to, or following, exposure to an OP,
wherein said 4R cembranoid, 4S cembranoid or cembranoid analogue is administered in an amount effective to protect said subject from said neuronal injury following exposure to said organophosphate, and
wherein the 4R cembranoid, 4S cembranoid or cembranoid analogue is administered with another neuroprotective agent selected from the group consisting of atropine, pralidoxime and midazolam.

2. The method of claim 1, wherein the neuronal injury is brain injury.

3. The method of claim 1, wherein the 4R cembranoid, 4S cembranoid or cembranoid analogue is administered prior to, or immediately after, an exposure to an OP-containing agent.

4. The method of claim 1, wherein the 4R cembranoid, 4S cembranoid or cembranoid analogue is administered with 1-10 mg/kg body weight of atropine.

5. A method for treating OP-induced neuronal damage in a subject, comprising: administering to the subject an effective amount of 4R cembranoid, 4S cembranoid or a cembranoid analogue following exposure to an organophosphate,
wherein said 4R cembranoid, 4S cembranoid or cembranoid analogue is administered in an amount effective to protect said subject from neuronal injury following exposure to said organophosphate.

6. The method of claim 5, wherein the 4R cembranoid, 4S cembranoid or cembranoid analogue is administered orally at a dose of 0.5-5 mg/kg body weight.

7. A method for treating OP-induced neuronal damage in a subject, comprising: administering to the subject 4R cembranoid following exposure to an organophosphate,
wherein said 4R cembranoid is administered in an amount effective to protect said subject from neuronal injury following exposure to said organophosphate.

8. The method of claim 7, wherein the 4R cembranoid is administered orally at a dose of 0.5-5 mg/kg body weight.

9. A neuroprotective pharmaceutical composition, comprising:
   4R cembranoid;
   atropine; and
   a pharmaceutically acceptable carrier.

* * * * *